(12) United States Patent
Shireman et al.

(10) Patent No.: US 8,222,566 B2
(45) Date of Patent: Jul. 17, 2012

(54) ELONGATED INTRACORPORAL MEDICAL DEVICE

(75) Inventors: Brice L. Shireman, Maple Grove, MN (US); Brian R. Reynolds, Ramsey, MN (US); Dave B. Johnson, Hopkins, MN (US); Alan D. Eskuri, Hanover, MN (US); Virgil F. Voeller, St. Louis Park, MN (US); Jeffrey A. Miller, Albertville, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1917 days.

(21) Appl. No.: 11/058,393

(22) Filed: Feb. 15, 2005

(65) Prior Publication Data

US 2005/0145307 A1 Jul. 7, 2005

Related U.S. Application Data

(63) Continuation of application No. 10/732,328, filed on Dec. 10, 2003, which is a continuation of application No. 10/376,068, filed on Feb. 26, 2003, now Pat. No. 7,182,735.

(51) Int. Cl.
  *B23K 26/00* (2006.01)
(52) U.S. Cl. .......... 219/121.85; 219/121.65; 219/121.66
(58) Field of Classification Search ............. 219/121.85, 219/121.65, 121.63, 121.66; 600/585
See application file for complete search history.

(56) References Cited

U.S. PATENT DOCUMENTS

| | | | |
|---|---|---|---|
| 3,174,851 A | 3/1965 | Buehler et al. |
| 3,351,463 A | 11/1967 | Rozner et al. |
| 3,753,700 A | 8/1973 | Harrison et al. |
| 4,006,874 A | 2/1977 | McGee |
| 4,763,647 A | 8/1988 | Gambale |
| 4,899,924 A | 2/1990 | Kawaguchi |
| 4,932,419 A | 6/1990 | de Toledo |
| 4,953,553 A | 9/1990 | Tremulis |
| 5,025,799 A | 6/1991 | Wilson |
| 5,135,503 A | 8/1992 | Abrams |
| 5,154,705 A | 10/1992 | Fleischhacker et al. |
| 5,165,421 A | 11/1992 | Fleischhacker et al. |
| 5,238,004 A | 8/1993 | Sahatjian et al. |
| 5,242,759 A | 9/1993 | Hall |
| 5,345,945 A | 9/1994 | Hodgson et al. |
| 5,368,661 A | 11/1994 | Nakamura et al. |
| 5,409,015 A | 4/1995 | Palermo |
| 5,411,476 A | 5/1995 | Abrams et al. |
| 5,429,139 A | 7/1995 | Sauter |
| 5,488,959 A | 2/1996 | Ales |
| 5,497,783 A | 3/1996 | Urick et al. |
| 5,520,194 A | 5/1996 | Miyata et al. |
| 5,551,444 A | 9/1996 | Finlayson |

(Continued)

FOREIGN PATENT DOCUMENTS

EP  0 267 141  5/1988

(Continued)

*Primary Examiner* — M. Alexandra Elve
(74) *Attorney, Agent, or Firm* — Seager, Tufte & Wickhem, LLC

(57) ABSTRACT

Alternative designs, materials and manufacturing methods for guidewires. Some embodiments pertain to a composite guidewire having proximal and distal section, and a connector adapted and configured for permanently joining the proximal section to the distal section. In some embodiments, at least one of the sections is made of a linear-elastic nickel-titanium alloy. Several alternative guidewire tip constructions and/or designs including methods and techniques of construction are also disclosed.

15 Claims, 6 Drawing Sheets

U.S. PATENT DOCUMENTS

| | | | |
|---|---|---|---|
| 5,605,162 A | 2/1997 | Mirzaee et al. |
| 5,636,642 A | 6/1997 | Palermo |
| 5,640,970 A | 6/1997 | Arenas |
| 5,664,580 A | 9/1997 | Erickson et al. |
| 5,666,969 A | 9/1997 | Urick et al. |
| 5,682,894 A | 11/1997 | Orr et al. |
| 5,695,111 A | 12/1997 | Nanis et al. |
| 5,706,826 A | 1/1998 | Schwager |
| 5,724,989 A | 3/1998 | Dobson |
| 5,749,837 A | 5/1998 | Palermo et al. |
| 5,769,796 A | 6/1998 | Palermo et al. |
| 5,772,609 A | 6/1998 | Nguyen et al. |
| 5,782,741 A | 7/1998 | Bradshaw et al. |
| 5,891,055 A | 4/1999 | Sauter |
| 5,954,672 A | 9/1999 | Schwager |
| 5,957,899 A | 9/1999 | Spears et al. |
| 5,957,903 A | 9/1999 | Mirzaee et al. |
| 6,019,736 A | 2/2000 | Avellanet et al. |
| 6,093,157 A | 7/2000 | Chandrasekaran |
| 6,106,488 A | 8/2000 | Fleming et al. |
| 6,139,510 A | 10/2000 | Palermo |
| 6,139,511 A | 10/2000 | Huter et al. |
| 6,139,540 A | 10/2000 | Rost et al. |
| 6,183,420 B1 | 2/2001 | Douk et al. |
| 6,203,505 B1 | 3/2001 | Jalisi et al. |
| 6,210,395 B1 | 4/2001 | Fleischhacker et al. |
| 6,306,105 B1 | 10/2001 | Rooney et al. |
| 6,348,041 B1 | 2/2002 | Klint |
| 6,383,146 B1 * | 5/2002 | Klint ........................... 600/585 |
| 6,387,060 B1 | 5/2002 | Jalisi |
| 6,410,886 B1 | 6/2002 | Julien |
| 6,428,489 B1 | 8/2002 | Jacobsen et al. |
| 6,482,166 B1 | 11/2002 | Fariabi |
| 6,500,130 B2 | 12/2002 | Kinsella et al. |
| 6,508,803 B1 | 1/2003 | Horikawa |
| 6,524,301 B1 | 2/2003 | Wilson et al. |
| 6,595,932 B2 | 7/2003 | Ferrera |
| 6,652,471 B2 | 11/2003 | Ehr et al. |
| 6,833,526 B2 * | 12/2004 | Sinkunas et al. ......... 219/121.66 |
| 6,905,503 B2 | 6/2005 | Gifford et al. |
| 7,153,277 B2 | 12/2006 | Skujins et al. |
| 2002/0007146 A1 | 1/2002 | Omaleki et al. |
| 2002/0013540 A1 | 1/2002 | Jacobsen et al. |
| 2002/0019599 A1 | 2/2002 | Rooney et al. |
| 2002/0032390 A1 | 3/2002 | Jafari |
| 2002/0095102 A1 | 7/2002 | Winters |
| 2003/0069520 A1 | 4/2003 | Skujins et al. |
| 2003/0069521 A1 | 4/2003 | Reynolds et al. |
| 2004/0142643 A1 | 7/2004 | Miller et al. |
| 2004/0167437 A1 | 8/2004 | Sharrow |
| 2004/0167441 A1 | 8/2004 | Reynolds et al. |

FOREIGN PATENT DOCUMENTS

| | | |
|---|---|---|
| EP | 0 274 412 | 7/1988 |
| EP | 0 383 159 | 8/1990 |
| EP | 0 739 641 | 10/1996 |
| EP | 0744186 | 11/1998 |
| EP | 0 381 810 | 8/1999 |
| EP | 0 940 123 | 9/1999 |
| EP | 1 256 408 | 11/2002 |
| EP | 0838230 | 9/2003 |
| JP | 4-292174 | 10/1992 |
| JP | 8052582 | 2/1996 |
| JP | 8-173547 | 7/1996 |
| JP | 2507463 | 8/1996 |
| JP | 8-243169 | 9/1996 |
| JP | 8-317989 | 12/1996 |
| JP | 9061730 | 3/1997 |
| WO | 9519800 | 7/1995 |
| WO | WO 96/23441 | 8/1996 |
| WO | WO 96/38195 | 12/1996 |
| WO | WO 98/18516 | 5/1998 |
| WO | WO 98/58697 | 12/1998 |
| WO | 9958183 | 11/1999 |
| WO | WO 02/05886 | 1/2002 |
| WO | WO 02/34324 | 5/2002 |
| WO | 02094366 | 11/2002 |

* cited by examiner

ELONGATED INTRACORPORAL MEDICAL DEVICE

CROSS REFERENCE TO CO-PENDING APPLICATIONS

This application is a continuation of U.S. application Ser. No. 10/732,328, filed Dec. 10, 2003; which is a continuation of U.S. application Ser. No. 10/376,068, filed Feb. 26, 2003 now U.S. Pat. No. 7,182,735, the disclosures of which are incorporated herein by reference.

FIELD OF TECHNOLOGY

The invention generally pertains to intracorporal medical devices, such as guidewires, catheters, or the like.

BACKGROUND

A wide variety of medical devices have been developed for intracorporal use. Elongated medical devices are commonly used in to facilitate navigation through and/or treatment within the anatomy of a patient. Because the anatomy of a patient may be very tortuous, it is desirable to combine a number of performance features in such devices. For example, it is sometimes desirable that the device have a relatively high level of pushability and torqueability, particularly near its proximal end. It is also sometimes desirable that a device be relatively flexible, particularly near its distal end. A number of different elongated medical device structures and assemblies are known, each having certain advantages and disadvantages. However, there is an ongoing need to provide alternative elongated medical device structures and assemblies.

SUMMARY OF SOME EMBODIMENTS

The invention provides several alternative designs, materials and methods of manufacturing alternative elongated medical device structures and assemblies.

BRIEF DESCRIPTION OF THE DRAWINGS

The invention may be more completely understood in consideration of the following detailed description of various embodiments of the invention in connection with the accompanying drawings, in which.

Figure 1:
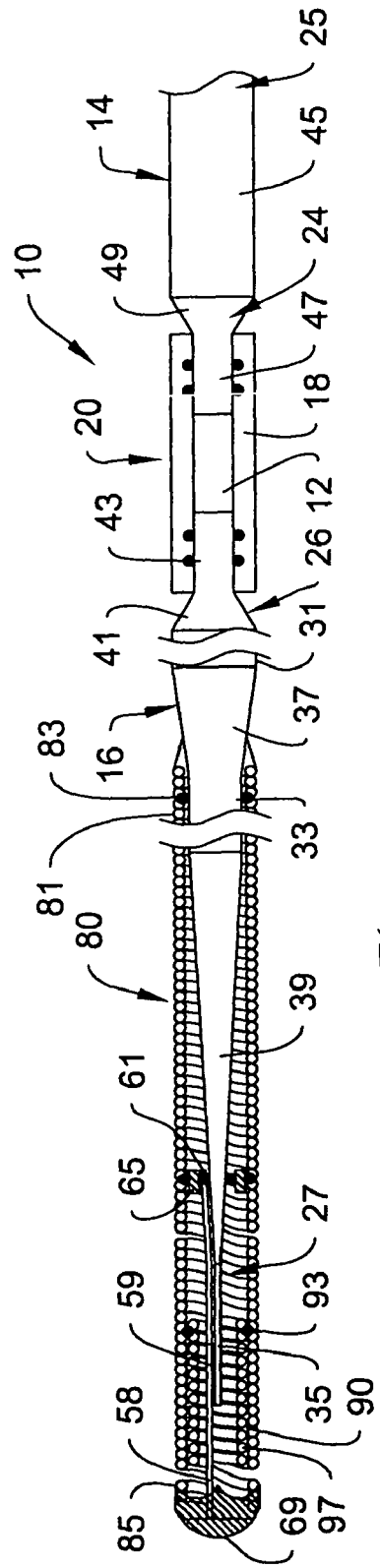
FIG. 1 is a partial cross sectional fragmentary view of a guidewire in accordance with one example embodiment.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF SOME EXAMPLE EMBODIMENTS

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

Weight percent, percent by weight, wt %, wt-%, % by weight, and the like are synonyms that refer to the concentration of a substance as the weight of that substance divided by the weight of the composition and multiplied by 100.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention. For example, although discussed with specific reference to guidewires in the particular embodiments described herein, the invention may be applicable to a variety of medical devices that are adapted to be advanced into the anatomy of a patient through an opening or lumen. For example, certain aspects of the invention may be applicable to fixed wire devices, catheters (e.g. balloon, stent delivery, etc.) drive shafts for rotational devices such as atherectomy catheters and IVUS catheters, endoscopic devices, laproscopic devices, embolic protection devices, spinal or cranial navigational or therapeutic devices, and other such devices.

Refer now to FIG. 1 which a is a partial cross sectional fragmentary view of a guidewire 10 including a proximal guidewire section 14 and a distal guidewire section 16. The proximal section 14 includes a distal end 24 and a proximal end 25, and the distal section 16 includes a proximal end 26 and a distal end 27. In this embodiment, the guidewire 10 includes a connection 20 joining the proximal guidewire section 14 and the distal guidewire section 16. The embodiment of FIG. 1 utilizes a joint 12 including a tubular connector 18. In some other embodiments, the guidewire 10 can include a shaft or core portion that can be one continuous member, for example, the proximal guidewire section 14 and a distal guidewire section 16 may be continuous with one another and, collectively, define a continuous shaft or core. In some other embodiments, the guidewire 10 can include a shaft or core portion that includes a plurality of sections connected by joints. As used herein, the proximal section 14 and the distal section 16 may generically refer to any two adjacent guidewire sections along any portion of the guidewire.

Those of skill in the art and others will recognize that the materials, structure, and dimensions of the proximal/distal guidewire sections 14/16 are dictated primary by the desired characteristics and function of the final guidewire, and that any of a broad range of materials, structures, and dimensions can be used.

For example, the proximal and distal guidewire sections 14/16 may be formed of any materials suitable for use, dependent upon the desired properties of the guidewire. Some examples of suitable materials include metals, metal alloys, polymers, or the like, or combinations or mixtures thereof. Some examples of suitable metals and metal alloys include stainless steel, such as 304V, 304L, and 316L stainless steel; alloys including nickel-titanium alloy such as linear elastic or superelastic (i.e. pseudoelastic) nitinol; nickel-chromium alloy; nickel-chromium-iron alloy; cobalt alloy; tungsten or tungsten alloys; MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); hastelloy; monel 400; inconel 625; or the like; or other suitable material, or combinations or alloys thereof. In some embodiments, it is desirable to use metals, or metal alloys that are suitable for metal joining techniques such as welding, soldering, brazing, crimping, friction fitting, adhesive bonding, etc.

The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL).

Within the family of commercially available nitinol alloys, is a category designated "linear elastic" which, although is similar in chemistry to conventional shape memory and superelastic (i.e. pseudoelastic) varieties, exhibits distinct and useful mechanical properties. By skilled applications of cold work, directional stress, and heat treatment, the wire is fabricated in such a way that it does not display a substantial "superelastic plateau" or "flag region" in its stress/strain curve. Instead, as recoverable strain increases, the stress continues to increase in an essentially linear relationship until plastic deformation begins. In some embodiments, the linear elastic nickel-titanium alloy is an alloy that does not show any martensite/austenite phase changes that are detectable by DSC and DMTA analysis over a large temperature range.

For example, in some embodiments, there are no martensite/austenite phase changes detectable by DSC and DMTA analysis in the range of about −60° C. to about 120° C. The mechanical bending properties of such material are therefore generally inert to the effect of temperature over this very broad range of temperature. In some particular embodiments, the mechanical properties of the alloy at ambient or room temperature are substantially the same as the mechanical properties at body temperature. In some embodiments, the use of the linear elastic nickel-titanium alloy allows the guidewire to exhibit superior "pushability" around tortuous anatomy.

In some embodiments, the linear elastic nickel-titanium alloy is in the range of about 50 to about 60 weight percent nickel, with the remainder being essentially titanium. In some particular embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of suitable nickel-titanium alloys include those disclosed in U.S. Pat. Nos. 5,238,004 and 6,508,803, which are incorporated herein by reference. In some other embodiments, a superelastic alloy, for example a superelastic nitinol can be used to achieve desired properties.

The entire guidewire 10 can be made of the same material, or in some embodiments, can include portions or sections, for example, proximal/distal guidewire sections 14/16, that are made of different materials. In some embodiments, the material used to construct different portions of the guidewire 10 can be chosen to impart varying flexibility and stiffness characteristics to different portions of the wire. For example, in some embodiments, the proximal guidewire section 14 may be formed of relatively stiff material such as straightened 304v stainless steel wire. Alternatively, proximal portion 14 may be comprised of a metal or metal alloy such as a nickel-titanium alloy, nickel-chromium alloy, nickel-chromium-iron alloy, cobalt alloy, or other suitable material. In general, the material used to construct proximal portion 14 may be selected to be relatively stiff for pushability and torqueability.

In some embodiments, the distal guidewire section 16 may be formed of a relatively flexible material such as a straightened super elastic (i.e. pseudoelastic) or linear elastic alloy (e.g., nickel-titanium), or alternatively, a polymer material, such as a high performance polymer. Alternatively, distal portion 16 may include a metal or metal alloy such as stainless steel, nickel-chromium alloy, nickel-chromium-iron alloy, cobalt alloy, or other suitable material. In general, the material used to construct distal portion 16 may be selected to be relatively flexible for trackability.

In at least some embodiments, portions or all of the proximal/distal guidewire sections 14/15, or other structures included within the guidewire 10 may also be doped with, coated or plated with, made of, or otherwise include a radiopaque material. Radiopaque materials are understood to be materials capable of producing a relatively bright image on a fluoroscopy screen or another imaging technique during a medical procedure. This relatively bright image aids the user of guidewire 10 in determining its location. Some examples of radiopaque materials can include, but are not limited to, gold, platinum, palladium, tantalum, tungsten alloy, polymer material loaded with a radiopaque filler, and the like, or combinations or alloys thereof.

In some embodiments, a degree of MRI compatibility is imparted into guidewire 10. For example, to enhance compatibility with Magnetic Resonance Imaging (MRI) machines, it may be desirable to make the proximal/distal guidewire sections 14/16, or other portions of guidewire 10, in a manner that would impart a degree of MRI compatibility. For example, the proximal/distal guidewire sections 14/16, or portions thereof, may be made of a material that does not substantially distort the image and create substantial artifacts (artifacts are gaps in the image). Certain ferromagnetic materials, for example, may not be suitable because they may create artifacts in an MRI image. The proximal/distal guidewire sections 14/16, or portions thereof, may also be made from a material that the MRI machine can image. Some materials that exhibit these characteristics include, for example, tungsten, Elgiloy, MP35N, nitinol, and the like, and others, or combinations or alloys thereof.

The length of proximal/distal guidewire sections 14/16 (and/or the length of guidewire 10) is typically dictated by the length and flexibility characteristics desired in the final medical device. For example, proximal section 14 may have a length in the range of about 20 to about 300 centimeters or more, the distal section 16 may have a length in the range of about 3 to about 50 centimeters or more, and the guidewire 10 may have a total length in the range of about 25 to about 350 centimeters or more. It can be appreciated that alterations in the length of sections 14/16 and guidewire 10 can be made without departing from the spirit of the invention.

Proximal/distal guidewire sections 14/16 can have a solid cross-section, but in some embodiments, can have a hollow cross-section. In yet other embodiments, guidewire sections 14/16 can include combinations of areas having solid cross-sections and hollow cross sections. Moreover, guidewire sections 14/16 can be made of rounded wire, flattened ribbon, or other such structures having various cross-sectional geometries. The cross-sectional geometries along the length of guidewire sections 14/16 can also be constant or can vary. For example, FIG. 1 depicts guidewire sections 14/16 as having a generally round cross-sectional shape. It can be appreciated that other cross-sectional shapes or combinations of shapes may be utilized without departing from the spirit of the invention. For example, the cross-sectional shape of guidewire sections 14/16 may be oval, rectangular, square, polygonal, and the like, or any suitable shape.

As shown in FIG. 1, guidewire sections 14/16 may include one or more tapers or tapered regions. The tapered regions may be linearly tapered, tapered in a curvilinear fashion, uniformly tapered, non-uniformly tapered, or tapered in a step-wise fashion. The angle of any such tapers can vary, depending upon the desired flexibility characteristics. The length of the taper may be selected to obtain a more (longer length) or less (shorter length) gradual transition in stiffness. It can be appreciated that essentially any portion of guidewire 10 and/or guidewire sections 14/16 may be tapered and the taper can be in either the proximal or the distal direction.

As shown in FIG. 1, the guidewire sections 14/16 may include one or more portions where the outside diameter is narrowing, and portions where the outside diameter remains essentially constant. The number, arrangement, size, and length of the narrowing and constant diameter portions can be varied to achieve the desired characteristics, such as flexibility and torque transmission characteristics.

The tapered and constant diameter portions of the tapered region may be formed by any one of a number of different techniques, for example, by centerless grinding methods, stamping methods, and the like. The centerless grinding technique may utilize an indexing system employing sensors (e.g., optical/reflective, magnetic) to avoid excessive grinding of the connection. In addition, the centerless grinding technique may utilize a CBN or diamond abrasive grinding wheel that is well shaped and dressed to avoid grabbing core wire during the grinding process. In some embodiments, distal shaft member 20 can be centerless ground using a Royal Master HI-AC centerless grinder. Some examples of suitable grinding methods are disclosed in U.S. patent application Ser. No. 10/346,698 filed Jan. 17, 2003, which is herein incorporated by reference.

The narrowing and constant diameter portions as shown in FIG. 1 are not intended to be limiting, and alterations of this arrangement can be made without departing from the spirit of the invention. One of skill will recognize that a guidewire core wire can have a profile different from that illustrated in FIG. 1.

In the embodiment shown in FIG. 1, the distal guidewire section 16 includes three constant diameter regions 31, 33, and 35, interconnected by two tapering regions 37 and 39. The constant diameter regions 31, 33, and 35 and tapering regions 37 and 39 are disposed such that the distal guidewire section 16 includes a geometry that decreases in cross sectional area toward the distal end thereof. In some embodiments, these constant diameter regions 31, 33, and 35 and tapering regions 37 and 39 are adapted and configured to obtain a transition in stiffness, and provide a desired flexibility characteristic. Also in some embodiments, portions of the guidewire section 16 can be flattened, for example, to provide for desired flexibility characteristics, or to provide an attachment point for other structure. For example, constant diameter portion 35 could include a portion thereof that is flattened.

The distal guidewire section 16 also includes tapered portion 41 and constant diameter portion 43 near its proximal end. This reduction in diameter near the proximal end is configured to accommodate the connector member 18 in this particular embodiment, as will be discussed in more detail below.

In the embodiment shown in FIG. 1, the proximal section 14 includes a proximal constant diameter portion 45, a distal constant diameter portion 47, and a taper portion 49 disposed there between. This reduction in diameter near the distal end the proximal section 14 is also configured to accommodate the connector member 18 in this particular embodiment, as will be discussed in more detail below.

It is to be understood that a broad variety of materials, dimensions and structures can be used to construct suitable embodiments, depending on the desired characteristics. The following examples of some dimensions are included by way of example only, are not intended to be limiting, and other dimensions out of the following ranges can be used.

In some example embodiments, the distal section 16 of the guidewire 10 can have a length in the range of about 3 to about 25 inches. The constant diameter regions 31, 33, and 35, can have outer diameters in the range of about 0.01 to about 0.015, about 0.005 to about 0.012 and about 0.001 to about 0.005 inches respectively, and lengths in the range of about 1 to about 10, about 1 to about 10 and about 0.1 to about 2 inches, respectively. The tapering regions 37 and 39 can have lengths in the range of about 0.5 to about 5, and about 0.5 to about 5 inches, respectively, and are generally linearly tapered. Additionally, the constant diameter portion 43 can have outer diameters in the range of about 0.005 to about 0.012 inches, and a length in the range of about 0.02 to about 1.5 inches. The tapered portion 41 can have a length in the range of about 0.02 to about 1 inches, and can be generally linearly tapered.

In some embodiments, as discussed above, a portion of the constant diameter portion 35 can be flattened, for example, the distal most about 0.05 to about 1 inch of the constant diameter portion 35 can be flattened to define generally parallel opposed surfaces, and to have a thickness in the range of about 0.0005 to about 0.0025 inches.

Also in some example embodiments, the proximal section 14 of the guidewire 10 can have a length in the range of about 30 to about 150 inches. The constant diameter regions 45 and 47 can have outer diameters in the range of about 0.01 to about 0.015 and about 0.005 to about 0.012 inches, respectively, and lengths in the range of about 30 to about 150, and about 0.02 to about 1.5 inches, respectively. The tapering section 49 can have a length in the range of about 0.02 to about 1 inch, and can be generally linearly tapered.

In some particular embodiments, the proximal guidewire section 14 is formed from a stainless steel wire, and the distal guidewire section 16 is formed from a linear elastic nitinol wire.

The distal end 24 of the proximal portion 14 and the proximal end 26 of distal portion 16 (i.e., the joined ends) may form a joint 12. Some methods and structures that can be used to interconnect different shaft sections are disclosed in U.S. Publication Nos. 2003/0069520 A1 and 2003/0069521 A1, which are incorporated herein by reference.

In some embodiments, the joined ends 24/26 are spaced, as shown in FIG. 1. In some embodiments, the joined ends 24/26 can be spaced a distance in the range of about 0 to about 1.5 inches within the connector member 18. Alternatively, the joined ends 24/26 may form a touching but joint, an overlapping tapered joint 12, an overlapping joint 12 that is not tapered, or the like. The end portions 24/26 may have a uniform profile (diameter), a bulbous portion for purposes of mechanical interlocking and the like, or a helical form for purposes of mechanical interlocking or the like. In embodiments where the end portions 24/26 overlap to form an overlapping joint, the overlapping joint can function to blend the stiffness of proximal portion 14 and distal portion 16 by combining the properties of each end section 24/26 making up the cross section of the overlapping joint. In some embodiments, the joint 12 can form a flexibility transition region that has a relative flexibility that is between the flexibility of the distal end 24 of the proximal portion 14 and the flexibility of the proximal end 26 of the distal portion 16.

As mentioned previously, the proximal guidewire section 14 and the distal guidewire section 16 may be formed of different materials (i.e., materials having different moduli of elasticity) resulting in a difference in flexibility. For example, the proximal guidewire section 14 may be formed of stainless steel wire and the distal guidewire section 16 may be formed of nickel-titanium alloy wire, both having the same dimensions near the joint, resulting in a 3:1 difference in elastic modulus. Such a difference in elastic modulus (i.e., flexibility) may result in a stress concentration point during flexure and/or torsion that may have a tendency to kink and fracture. By virtue of the gradual transition in stiffness provided in some embodiments by the joint 12, stress is distributed along the entire length of the connection 20 thereby decreasing the probability that guidewire 10 may kink at the junction.

A gradual transition in stiffness may also allow the connection 20 to be located further distally. According to this embodiment, the distal portion 16 may be manufactured to be shorter than proximal portion 14. Including a relatively long proximal section 14 may advantageously increase the torquability and pushability of the guidewire 10. Although only one connection 20 is shown, additional connections 20 may be used to connect other guidewire sections of varying stiffness.

The connector 18 may comprise a tubular structure such as a hypotube as shown or a coiled wire. The connector 18 may have an inside diameter sized appropriately to receive the ends 24/26 of the proximal portion 14 and the distal portion 16, and an outside diameter sufficient to accommodate a final grinding procedure. In some example embodiments, the connector 18 can have an inner diameter in the range of about 0.004 to about 0.02 inches, and an outer diameter in the range of about 0.01 to about 0.02 inches. The final diameter of the guidewire 10 and the connector 18 may be in the range of 0.010 to 0.018 inches, for example. By way of example, not limitation, the connector 18 may have a length of about 0.03 to 3.0 inches. However, in some other embodiments, this type of construction can be applied to wires of larger diameter intended, for example, for peripheral intervention purposes. Such wires could range as large as 0.035 inches in diameter or larger, and therefore have an extended length connector and correspondingly longer overlapping sections. The diameters given, as with the other specific dimensional information given herein, are by way of example only.

In some embodiments, the lateral flexibility, bendability or other such characteristics of the connector 18 can be achieved or enhanced in a number of ways. For example, the materials selected for the connector 18 may be chosen so that the connector 18 has a desired lateral flexibility. For example, in some embodiments, it may be desirable that the connector 18 has a greater lateral flexibility than the lateral flexibilities of proximal guidewire section 14 adjacent distal end 24 and distal guidewire section 16 adjacent proximal end 26. For example, the connector 18 may be formed of materials having a different modulus of elasticity than the adjacent portions of the guidewire members 14/16, resulting in a difference in flexibility.

In addition to, or as an alternative to material composition, the desired lateral flexibility or bending characteristics can be imparted or enhanced by the structure of the connector 18. For example, a plurality of grooves, cuts, slits, or slots can be formed in a tubular connector 18. Such structure may be desirable because they may allow connector 18 to be bendable as well as transmit torque and pushing forces from proximal section 14 to distal section 16. The cuts or slots or grooves can be formed in essentially any known way. For example, cuts, grooves or slots can be formed by mechanical methods, such as micro machining, saw cutting, LASER cutting, chemically etching, treating or milling, casting, molding, other known methods, and the like. In some embodiments, cuts, grooves, or slots can completely penetrate connector 18. In other embodiments, cuts, grooves, or slots may only partially extend into connector 18, or include combinations of both complete and partial cuts.

The arrangement of such cuts, grooves, or slots may vary. For example, the cuts, grooves, or slots may be formed such that one or more spines, splines, or beams are formed in the tubular connector 18. Such spines or beams could include portions of the tubular member that remain after the cuts or slots are formed in the body of the tubular member. Such spines or beams can act to maintain a relatively high degree of tortional stiffness, while maintaining a desired level of lateral flexibility. In some embodiments, some adjacent cuts or slots can be formed such that they include portions that overlap with each other about the circumference of the tube. In other embodiments, some adjacent slots or cuts can be disposed such that they do not necessarily overlap with each other, but are disposed in a pattern that provides the desired degree of lateral flexibility.

Additionally, the size, shape, spacing, or orientation of the cuts or slots, or in some embodiments, the associated spines or beams, can be varied to achieve the desired lateral flexibility and/or tortional rigidity characteristics of the connector 18. The number or density of the cuts or slots along the length of the connector 18 may vary, depending upon the desired characteristics. For example, the number or proximity of slots to one another near the midpoint of the length of the connector 18 may be high, while the number or proximity of slots to one another near either the distal or proximal end of the connector 18, or both, may be relatively low, or vice versa. Collectively, this description illustrates that changes in the arrangement, number, and configuration of slots may vary without departing from the scope of the invention. Some additional examples of arrangements of cuts or slots formed in a tubular body are disclosed in U.S. Pat. No. 6,428,489; in U.S. Publication No. 2002/0013540 A1; and in a U.S. application Ser. No. 10/375,493, filed on Feb. 26, 2003 and entitled "ARTICULATING INTRACORPORAL MEDICAL DEVICE", all of which are incorporated herein by reference.

The connector 18 may be made of or include a metal, metal alloy, polymer, metal-polymer composite, or the like, as discussed above with regard to the guidewire sections 14/16, and may include radiopaque materials or include materials or structure to impart a degree of MRI compatibility, as discussed above with regard to the guidewire sections 14/16.

Some types of alloys are particularly suitable for connector 18 for some purposes, for example, for connecting a stainless steel proximal section 14 and a nickel titanium alloy distal section 16, or visa-versa. An example is a nickel-chromium-iron alloy designated UNS N06625 and is available under the trade name INCONEL 625, which advantageously welds to both stainless steels and nickel-titanium alloys. INCONEL 625 wire may be obtained from California Fine Wire Company of Grover Beach, Calif. Another example of a suitable alloy which welds to both stainless steels and nickel-titanium alloys is designated UNS 10276 and is available under the trade name ALLOY C276 from Fort Wayne Metals Research Products Corporation of Fort Wayne, Ind. Another example of a suitable alloy which welds to both stainless steels and nickel-titanium alloys is of the Hastelloy family and an example of which is available under the trade name ALLOY B2 from Fort Wayne Metals Research Products Corporation of Fort Wayne, Ind. In some embodiments, where for example, a welding process is used to connect the connector 18, for example, to a stainless steels proximal section 14 and a nickel-titanium proximal section 6, it can be beneficial to use an alloy material for the connector 18 that can be welded to both stainless steel and a nickel titanium alloy.

To manufacture the connection 20 of the guidewire 10, the ends 24/26 of the proximal and distal guidewire sections 14/16 may be ground to form the desired shape to accommodate the connector. For example, a recess step, such as constant diameter portions 43/47 and taper portions 41/49 may be ground or otherwise formed into the proximal and distal guidewire sections 14/16 to accommodate the connector tube 18. If a connector tube 18 is not to be used, such a recess step need not be ground.

For the embodiments utilizing a connector tube 18, the connector tube 18 is positioned over one of the ends 24/26 of the proximal and distal guidewire sections 14/16. The proximal and distal guidewire sections 14/16 and the connector tube 18 may be bonded, welded (e.g., resistance or LASER welded), soldered (e.g. LASER diode soldering), brazed, or otherwise connected by a suitable technique depending on the material selected for each component. Additionally, in some other example embodiments, securing the connector 18 to the proximal and distal sections 14/16 may include the use of a connector and/or an expandable alloy, for example, a bismuth alloy. Some examples of methods, techniques and structures that can be used to interconnect different portions of a guidewire using such expandable material are disclosed in a U.S. patent application Ser. No. 10/375,766, filed on Feb. 26, 2003 and entitled "Composite Medical Device", which is hereby incorporated by reference. Alternatively, the ends 24/26 and the connector tube 18 may be crimped together or may be sized to establish a friction fit therebetween. If a connector tube 18 is not used, the ends 24/26 may be bonded, welded (e.g., resistance or LASER welded), soldered, brazed, or otherwise connected, using a connector material. Connector material may be the same as or similar to the material of the connector 18. In all cases, because the connection 20 may reside within a catheter lumen or within the anatomy during use, it is preferred that a permanent connection (as opposed to a releasable connection) be used.

In some particular embodiments, the connector 18 is welded to proximal and distal guidewire sections 14/16. It is to be appreciated that various welding processes can be utilized. In general, welding refers to a process in which two materials such as metal or metal alloys are joined together by heating the two materials sufficiently to at least partially melt adjoining surfaces of each material. A variety of heat sources can be used to melt the adjoining materials. Examples of welding processes that can be suitable in some embodiments include LASER welding, resistance welding, TIG welding, microplasma welding, electron beam, and friction or inertia welding.

LASER welding equipment which may be suitable in some applications is commercially available from Unitek Miyachi of Monrovia, Calif. and Rofin-Sinar Incorporated of Plymouth, Mich. Resistance welding equipment which may be suitable in some applications is commercially available from Palomar Products Incorporated of Carlsbad, Calif. and Polaris Electronics of Olathe, Kans. TIG welding equipment which may be suitable in some applications is commercially available from Weldlogic Incorporated of Newbury Park, Calif. Microplasma welding equipment which may be suitable in some applications is commercially available from Process Welding Systems Incorporated of Smyrna, Tenn.

In some embodiments, LASER or plasma welding can be used to secure the connector 18 and the proximal and distal guidewire sections 14/16 securely together. In LASER welding, a light beam is used to supply the necessary heat. LASER welding can be beneficial in the processes contemplated by the invention, as the use of a LASER light heat source can provide pinpoint accuracy. It should also be understood that such LASER welding can also be used to attach other components of the guidewire, as discussed below.

Additionally, in some embodiments, LASER energy can be used as the heat source for soldering, brazing, or the like for attaching different components or structures of the guidewire together. Again, the use of a LASER as a heat source for such connection techniques can be beneficial, as the use of a LASER light heat source can provide pinpoint accuracy. One particular example of such a technique includes LASER diode soldering.

In some embodiments, the connection can extend around the entire circumference of the connector 18 and the proximal and distal guidewire sections 14/16. In some other embodiments, however, one or more spaced connection points can be made around the circumference of the proximal and distal guidewire sections 14/16. The use of certain attachment techniques, for example laser welding or laser diode soldering, or the like, can be useful in making connections around only a portion of the circumference because they tend to allow the accuracy needed to make such connections.

Once connected, the connector tube 18 and the proximal and distal guidewire sections 14/16 can be centerless ground or otherwise shaped or formed as desired to provide the desired characteristics, for example, a smooth and uniform profile across the connection 20, or to straighten out small misalignments between the proximal and distal guidewire sections 14/16. Other portions of the guidewire 10 may be ground as well to provide the desired tapers and changes in diameter.

Once finally formed or ground, in some embodiments, a flexible coil tip and/or a polymer jacket tip (optionally covering connection 20) or combination thereof, and other such structure, such as radiopaque markers, safety and/or shaping ribbons (coiled or uncoiled), and the like, may be placed on the guidewire 10. Some examples of additional components and tip constructions are disclosed in U.S. Publication Nos. 2003/0069520 A1 and 2003/0069521 A1, which are incorporated herein by reference. Additionally, in some embodiments, a coating, for example a lubricious (e.g., hydrophylic) or other type of coating may be applied to all or portions of the guidewire. Different coatings can be applied to different sections of the guidewire. Some examples of such coatings and materials and methods used to create such coatings can be found in U.S. Pat. Nos. 6,139,510 and 5,772,609, which are incorporated herein by reference.

For example, the embodiment in FIG. 1 includes a wire or ribbon 58 that is attached adjacent the distal end 27 of the distal section 16, and extends distally of the distal end 27. In some embodiments, the wire or ribbon 58 can be a fabricated or formed wire structure, for example a coiled wire. In the embodiment shown however, the ribbon 58 is a generally straight ribbon that overlaps with and is attached to the distal end 27 of the distal section 16.

The ribbon 58 can be made of any suitable material and sized appropriately to give the desired characteristics, such as strength and flexibility characteristics. Some examples of suitable materials include metals, metal alloys, polymers, and the like, and may include radiopaque materials or include materials or structure to impart a degree of MRI compatibility, as discussed above in relation to the proximal and distal guidewire sections 14/16, and in relation to the connector 18.

The following examples of some dimensions are included by way of example only, and are not intended to be limiting.

In some embodiments, the ribbon 58 is a flattened ribbon having a width in the range of about 0.002 to about 0.008 inches, a thickness in the rang of about 0.0005 to about 0.003 inches, and a length in the range of about 0.25 to about 3 inches. In some embodiments, the ribbon 58 overlaps with the distal section 16 by a length in the range of about 0.25 to about 2 inches, and includes a distal portion that extends distally beyond the distal section 16 by a length in the range of about 0.1 to about 2 inches.

The ribbon 58 can be attached to the distal section 16 using any suitable attachment technique. Some examples of attachment techniques include soldering, brazing, welding, adhesive bonding, crimping, or the like. In some embodiments, the ribbon or wire 58 can function as a shaping structure or a safety structure. The distal end of the ribbon 58 can be free of attachment, or can be attached to another structure, for example a tip portion 69, for example, a rounded tip portion. The tip portion 69 can be made or formed of any suitable material, for example a solder tip, a polymer tip, a welded tip, and the like, using suitable techniques.

In the embodiment shown in FIG. 1, the ribbon 58 is attached to the distal section 16 adjacent the distal end 27 thereof at two attachment points, 59 and 61. Attachment point 59 is disposed adjacent constant diameter region 35, which may or may not be flattened, as discussed above. In some embodiments, the attachment point 59 is disposed at the very distal end 27 of the distal section 16, while in other embodiments, the attachment point can be spaced more proximally form the very distal end 27. In some embodiments, attachment adjacent the very distal end 27 is used such that the distal end 27 of the section 16 and the ribbon can flex as one connected or integral unit. Such an arrangement can provide for desirable trackability characteristics, and can provide for desirable tip resiliency characteristics.

Attachment point 61 is disposed adjacent tapering region 39. It should be understood, however, that these attachment points and attachment techniques are given by way of example only, and that the ribbon can be attached at different locations and by using more or fewer attachment points, and a variety of attachment techniques, as desired, without parting from the spirit and scope of the invention.

Figure 3:
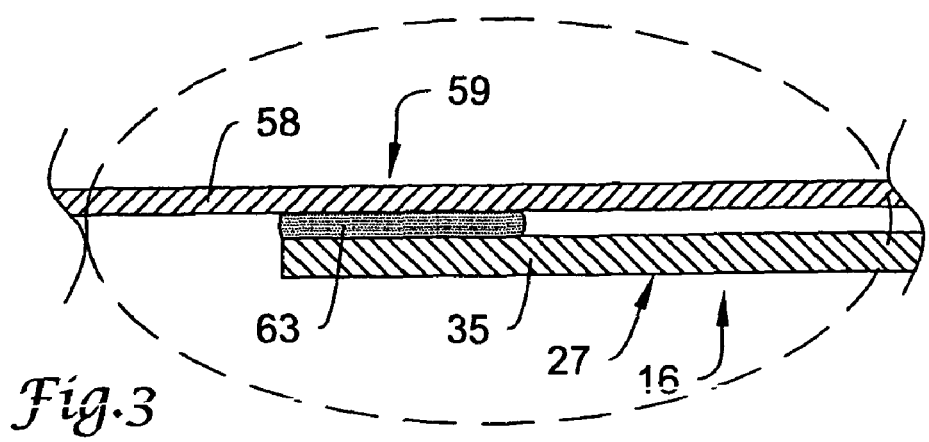
FIG. 3 is a cross sectional view of the ribbon of the guidewire of FIG. 1 which is attached to the distal section of the guidewire at a distal attachment point, for example, using solder and radiant heat energy to heat the solder, wherein the dotted lines indicate the area that might be heated using radiant heat energy.
Figure 4:
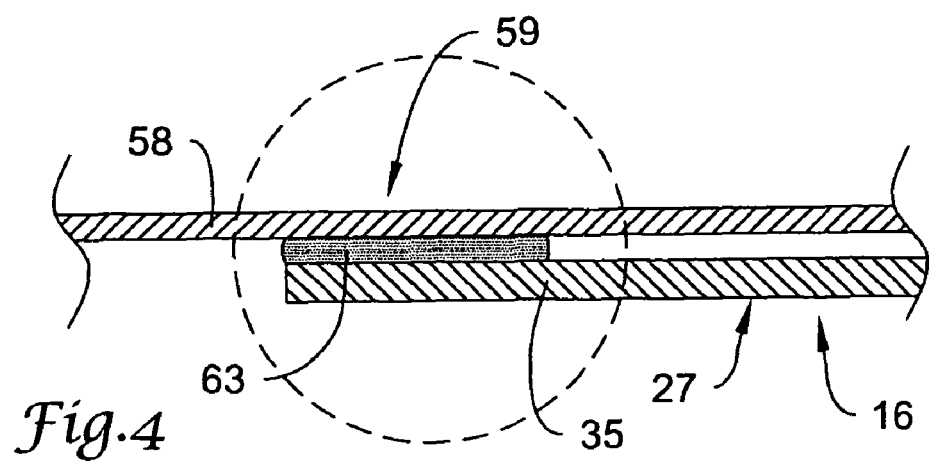
FIG. 4 is a cross sectional view of the ribbon of the guidewire of FIG. 1 which is attached to the distal section of the guidewire at a distal attachment point, for example, using solder and light source energy to heat the solder, wherein the dotted lines indicate the area that might be heated using light source energy.
Figure 5:
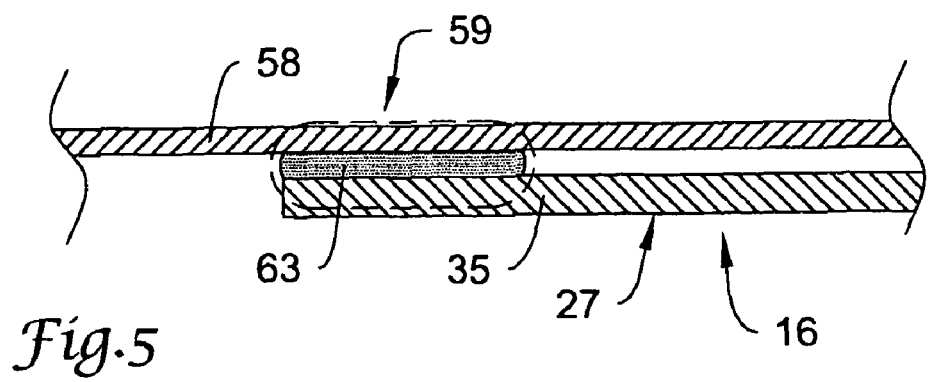
FIG. 5 is a cross sectional view of the ribbon of the guidewire of FIG. 1 which is attached to the distal section of the guidewire at a distal attachment point, for example, using solder and LASER energy to heat the solder, wherein the dotted lines indicate the area that might be heated using LASER energy.

Refer now to FIGS. 3-5 for a discussion of some particular attachment techniques that can be used. FIGS. 3-5 are close up cross sectional views of the guidewire of FIG. 1 about attachment point 59. In each of these Figures, the ribbon 58 is attached to the constant diameter region 35 adjacent the distal end 27 of the distal section 16 using a heat activated attachment material, for example a solder material 63, a brazing material, or other such material.

FIG. 3 is included to illustrate the use of a broad heat source, for example, a radiant heat source, to heat and activate the solder material 63 to make the connection. The dotted lines indicate the area that might be heated using such radiant heat energy. As can be seen, the entire area surrounding the attachment point 59 would be heated. In some embodiments, this can be undesirable. For example, if some of the components of the guidewire are heat sensitive materials, the heat may adversely affect the characteristics of the material. One example of such materials include some nickel titanium alloys, which if exposed to undue heat above a certain point, may undergo a phase change, or may anneal, which may effect the desired properties of the material.

FIG. 4 is similar to FIG. 3, but is included to illustrate the use of a narrower, or more controlled heat source, for example, light source energy, to heat the solder 63, wherein the dotted lines indicate the area that might be heated using light source energy. As can be seen, although the area affected is narrower than using a radiant heat source, as describe with reference to FIG. 3, the light source energy may still undesirably heat areas surrounding the attachment point 59.

FIG. 5 is similar to FIGS. 3 and 4, but is included to illustrate the use of an even narrower, or more controlled heat source, for example, a LASER energy source, to heat the solder 63, wherein the dotted lines indicate the area that might be heated using LASER source energy. As can be seen, the area affected is narrower than using a radiant heat source, or light source energy. Therefore, the use of LASER energy may be desirable to avoid undesirably heating larger areas surrounding the attachment point 59. The use of a LASER as a heat source in soldering, brazing, and the like, can be beneficial in the processes contemplated by the invention, as the use of a LASER light heat source can provide pinpoint accuracy. It should also be understood that such LASER soldering or brazing, or the like, can also be used to attach other components of the guidewire. One additional example of a process that uses LASER energy is diode soldering, which can also be used.

In some embodiments, the structures being connected can be pre-treated and/or pre-coated with a suitable attachment material prior to attachment. For example, the ribbon 58, or portions thereof, and/or the distal section 16, or portions thereof, or both, can be cleaned or treated to remove impurities or oxides. This can be useful, especially when one or both of the materials being connected is a difficult material to solder or braze to, such as some nickel titanium alloys. Some examples of such treatments include acid baths or washes, fluxing, pickling, pre-tinning, pre-plating (i.e. plating with another material) and the like. In some embodiments, one or both of the surfaces to be connected can be cleaned and pre-plated with another metallic material, for example, a nickel plating. In some embodiments, the surface to be soldered or brazed is treated with a molten alkali metal hydroxide, and then pre-treated, or "pre-tinned" with a suitable solder or brazing material. It should also be understood within the context of this disclosure that when a heat activated attachment material, such as solder or brazing material, is used to connect two components, such heat activated attachment material can be predisposed on the components being connected using such processes or treatments, or can be separately disposed or added to make the connection. Therefore, the heat activated attachment material used for making such connections can come form either source ("pre-tinned" or "added"), or from both sources. The heat activated attachment material can include any suitable, brazing material, or the like. Some examples of suitable solder or brazing material include, but are not limited to, tin based materials, for example, gold-tin solder, silver-tin solder, and the like, and many others.

Figure 6:
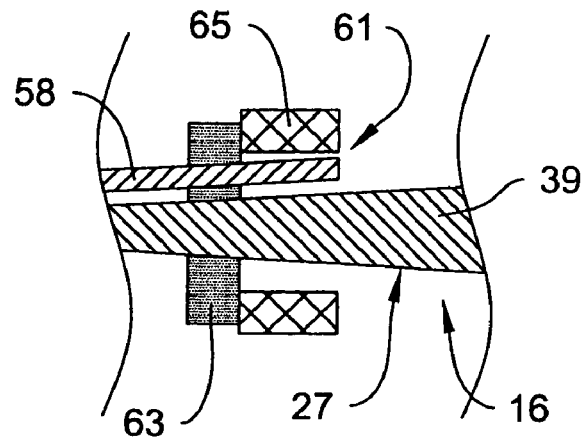
FIG. 6 is a cross sectional view of the proximal section of the ribbon of the guidewire of FIG. 1 prior to attachment to the distal section of the guidewire at a proximal attachment point, showing an attachment or centering ring, and solder material prior to heating.
Figure 7:
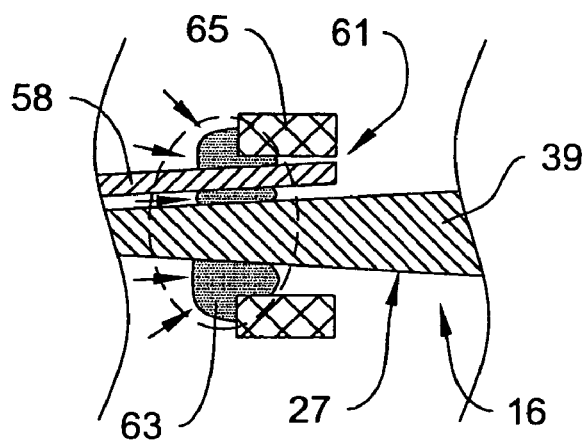
FIG. 7 is a cross sectional view of the ribbon of the guidewire of FIG. 6 during heating, showing the solder material flowing or wicking into the attachment points to attach the ribbon to the distal portion of the guidewire and to the attachment or centering ring.
Figure 8:
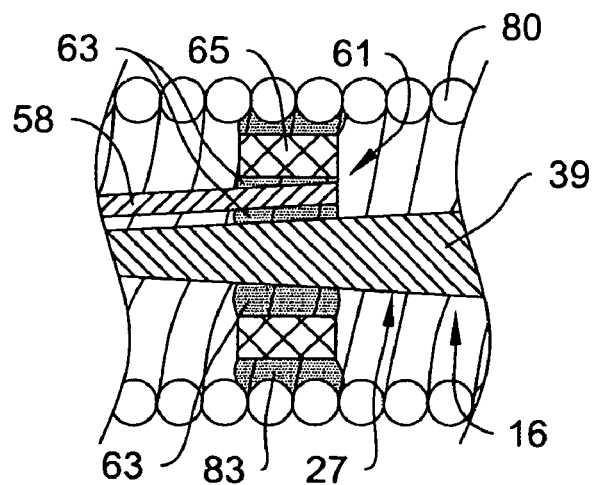
FIG. 8 is a cross sectional view of the ribbon of the guidewire of FIG. 7 after heating, showing the solder attachment points attaching the ribbon to the distal portion of the guidewire and to the attachment or centering ring, and also showing the coil attached to the centering ring.

Refer now to FIGS. 6-8 for a discussion of some additional particular attachment techniques that can be used. FIGS. 6 and 7 are close up cross sectional views of the distal guidewire section 16 of the guidewire of FIG. 1 at attachment point 61 prior to and during an attachment procedure. FIG. 8 is a close up cross sectional view of the distal guidewire section 16 of FIG. 1 at attachment point 61 after attachment of the ribbon 58 to the distal section 16. In each of these Figures, the ribbon 58 is being attached to the tapering region 39 adjacent the distal end 27 of the distal section 16 using a heat activated attachment material, for example a solder 63, a brazing material, or other such material. Additionally, an attachment or centering ring 65 is also being attached to the tapering region 39.

FIG. 6 shows an attachment or centering ring 65 that is disposed about the distal section 16, and the ribbon 58 is disposed between the centering ring 65 and the distal section 16. The centering ring 65 can be a generally tubular member that is adapted or configured to fit over a portion of the distal section 16, and in at least some embodiments, is adapted or configured to attach to the ribbon 58 and the distal section 16. Additionally, the centering ring 65 can be adapted and configured to attach to an outer member, such as a coil 80, as discussed in more detail below. In some embodiments, prior to attachment, as shown in FIG. 6, heat activated bonding or filler material, such as solder material 63, can be disposed adjacent to the centering ring 65. For example, solder material 63 can be disposed about the distal section 16, adjacent to the centering ring 65 and the ribbon 58. It should be understood however, that in other embodiments, the solder material 63 can be disposed or located at a different location than shown, for example, adjacent the proximal side of the centering ring 65, or alternatively, could be disposed in the desired attachment positions between the members to be connected prior to connection.

As shown in FIG. 7, the solder material 63 can then be heated using an appropriate heat source, and it will begin to flow into an attachment position between the ribbon and the distal section 16, and/or between the ribbon 58 and the centering ring 65, and/or between the distal section 16 and the centering ring 65, or all of the above positions. Some examples of suitable heat sources for use in soldering or brazing are described above. However, in some embodiments, LASER energy is used as the heat source to provide for accuracy of heating, and to avoid undesirable heating of structures adjacent the attachment points.

FIG. 8 shows the solder material 63 disposed in attachment positions that connect the ribbon 58 to the distal section 16, connect the ribbon 58 to the centering ring 65, and connect the distal section 16 to the centering ring 65. FIG. 8 also shows a coil 80 that has been attached to the centering ring 65, as will be discussed in more detail below.

It should be understood that the components being attached using such a technique, prior to attachment, can undergo treatments such as acid baths or washes, fluxing, pickling, pre-tinning, and the like, as described above.

It should also be understood that the above described attachment techniques are merely illustrative, and that other suitable attachment techniques or structures can be used. Additionally, the attachment techniques described above can be used at other locations along the length of the guidewire, or can be used to attach other components of the guidewire to each other. For example, a ring, such as attachment or centering ring 65, can be used to attach coils, ribbons, braids, wires, or the like, or other such structures to the proximal or distal guidewire sections 14/16. Additionally, the soldering or brazing techniques, for example, the use of LASER energy as the heat source, can be used in attaching additional structures to proximal or distal guidewire sections 14/16.

The embodiment in FIG. 1 also includes a coil 80 disposed about at least a portion of the proximal and/or distal guidewire sections 14/16. In the particular embodiment shown, the coil 80 can extend about the distal sections 16 from a point adjacent the tapering region 37 distally to a point beyond the distal most portion of the distal section 16. The coil 80 is attached to the distal guidewire section 16 at its proximal end 81 at attachment point 83 using any suitable attachment technique, for example soldering, brazing, welding, adhesive bonding, crimping, or the like. The distal end 85 of the coil 80 can be attached to the ribbon 58 via the rounded tip portion 69. As discussed above, the rounded tip portion 29 can be made of any suitable material, for example a solder tip, a polymer tip, and the like. In some other embodiments, the distal end 85 may be attached to other structure, for example, a spacer member or attachment or centering ring, or may be free of attachment. Additionally, the coil 80 can be attached at one or more intermediate points, for example, to the centering or attachment ring 65. For example, refer to FIG. 8, which shows the coil 80 attached to the centering or attachment ring 65.

The centering ring 65 can function to attach the coil 80 to the guidewire section 16, and can also function to somewhat maintain the axial and lateral position of the coil 80 relative to the guidewire section 16. Attachment to the centering ring 64 can also be performed using any suitable attachment technique, for example soldering (e.g. LASER diode soldering), brazing, welding, adhesive bonding, crimping, or the like.

It should be understood, however, that these attachment points are given by way of example only, and that the coil 80 can be attached at different locations and by using more or fewer attachment points, as desired, without parting from the spirit and scope of the invention. Additionally, in other embodiments, the coil 80 can be disposed at other locations along the length of the guidewire 10, or could extend the entire length of the guidewire 10.

In some embodiments, attachment of the coil 80 at either attachment point 83, at centering or attachment ring 65, or at other locations along the length of the guidewire 10 can be achieved using a welding process, for example, LASER or plasma welding. Any of the above described material, structure, techniques or equipment can be used. As described above, in LASER welding, a light beam is used to supply the necessary heat. LASER welding can be beneficial in the processes contemplated by the invention, as the use of a LASER light heat source can provide pinpoint accuracy. It should also be understood that such LASER welding can also be used to attach other components of the guidewire, as discussed above.

In some embodiments, the connection of the coil 80 at either attachment point 83, or at centering ring 65, can extend around the entire circumference of the coil 80. In some other embodiments, however, one or more spaced connection points that do not extend all the way around the circumference of the coil 80 can be made. The use of certain attachment techniques, for example laser welding or laser diode soldering, or the like, can be useful in making connections around only a portion of the circumference coil 80 because they tend to allow the accuracy needed to make such connections. In some embodiments, connections around only a portion of the circumference coil 80 can allow for some desired characteristics, such as increased flexibility of the coil 80.

Additionally, in some embodiments, a transition structure or layer can be disposed on the distal guidewire section 16 just proximal of the attachment point 83 to provide for a smooth transition between the outer surface of the distal section 16 and the coil 80. Any suitable material can be used, for example, an adhesive, a polymer, solder, or other such material.

Figure 14:
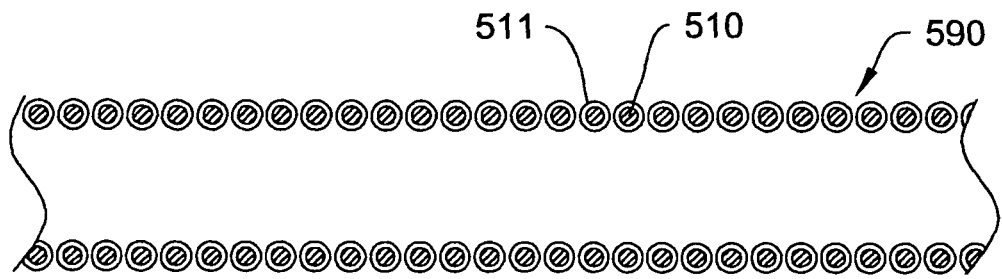
FIG. 14 is a cross sectional fragmentary view of an example coil that can be used in medical devices, the coil including a wire including an inner portion made of a first material and an outer portion made of a second material.

The coil 80 may be made of a variety of materials including metals, metal alloys, polymers, and the like, including those described above with regard to the guidewire sections 14/16, the connector 18, and the ribbon 58. Some examples of some suitable materials include stainless steel, such as 304V, 304L, and 316L stainless steel; alloys including nickel-titanium alloy such as linear elastic or superelastic (i.e. pseudoelastic) nitinol; nickel-chromium alloy; nickel-chromium-iron alloy; cobalt alloy; tungsten or tungsten alloys; MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); hastelloy; monel 400; inconel 625; or the like; or other suitable material. In some embodiments, the coil 80 can be made of, coated or plated with, or otherwise include a radiopaque material such as gold, platinum, tungsten, or the like, or combinations or alloys thereof, or polymer materials including radiopaque materials. Additionally, the coil can include materials or structure to impart a degree of MRI compatibility, as discussed above in relation to the guidewire sections 14/16, the connector 18, and the ribbon 58. For example, refer to FIG. 14, which is a cross sectional fragmentary view of an example coil 590 that can be used in medical devices, such as guidewires, wherein the coil 590 includes an inner portion, layer, or wire 510 that includes or is made of a first material, and an outer portion, layer, or wire 511 that includes or is made of a second material. For example, the inner portion 510 could be a wire or ribbon as discussed above, and the outer portion 511 could be a coating, cladding, plating, or extrusion of a radiopaque material or an MRI compatible imaging material, as discussed above.

Referring back to FIG. 1, the coil 80 may be formed of round wire or flat ribbon ranging in dimensions to achieve the desired flexibility. It can also be appreciated that other cross-sectional shapes or combinations of shapes may be utilized without departing from the spirit of the invention. For example, the cross-sectional shape of wires or filaments used to make the coil may be oval, rectangular, square, triangle, polygonal, and the like, or any suitable shape.

The coil 80 can be wrapped in a helical fashion by conventional winding techniques. The pitch of adjacent turns of coil 80 may be tightly wrapped so that each turn touches the succeeding turn or the pitch may be set such that coil 80 is wrapped in an open fashion. In some embodiments, the coil can have a pitch of up to about 0.04 inches, in some embodiments a pitch of up to about 0.02 inches, and in some embodiments, a pitch in the range of about 0.001 to about 0.004 inches. The pitch can be constant throughout the length of the coil 458, or can vary, depending upon the desired characteristics, for example flexibility. These changes in coil pitch can be achieved during the initial winding of the wire, or can be achieved by manipulating the coil after winding or after attachment to the guidewire. For example, in some embodiments, after attachment of the coil 80 to the guidewire 10, a larger pitch can be achieved on the distal portion of the coil 80 by simply pulling the coil.

Additionally, in some embodiments, portions or all of the coil 80 can include coil windings that are pre-tensioned or pre-loaded during wrapping, such that each adjacent coil winding is biased against the other adjacent coil windings to form a tight wrap. Such preloading could be imparted over portions of, or over the entire length of the coil 80.

The diameter of the coil 80 is preferably sized to fit around and mate with the guidewire 10, and to give the desired characteristics. The diameter of the coil 80 can be constant or tapered. In some embodiments, the coil 80 is tapered, for example, to mate with a tapered section of the guidewire 10, or with other structure. The diameter of the coil 80 can also include a taper beyond the distal end of the guidewire section 16, as desired.

It will be understood by those of skill in the art and others that a broad variety of materials, dimensions, and structures can be used to construct suitable embodiments, depending upon the desired characteristics. The following examples are included by way of example only, and are not intended to be limiting. The coil 80 can be in the range of about 1 to about 20 inches long, and is made of rounded wire having a diameter of about 0.001 to about 0.004 inches. The coil 80 can have an outer diameter that is generally constant, and is in the range of about 0.01 to about 0.015 inches. The inner diameter of the coil can also be generally constant, and is in the range of about 0.004 to about 0.013 inches. The pitch of the coil 80 can be in the range of about 0.0005 to about 0.05 inches.

In FIG. 1, the guidewire 10 also includes an inner coil 90 to form a dual coil tip construction. One or more additional inner coils could be included in other embodiments. The inner coil 90 is disposed about the distal end portion 27 of the distal guidewire section 16, and is disposed within the lumen of the outer coil 80. The inner coil 90 can be made of the same materials, and have the same general construction and pitch spacing as discussed above with regard to the outer coil 80. The inner coil, however, would include an outer diameter that allows it to fit within the lumen of the outer coil 80, and in some embodiments, has an outer diameter that allows it be disposed in a relatively snug or tight fit with the inner diameter of the outer coil 80. In some embodiments, the inner coil 90 can be made of a radiopaque wire, for example, a platinum/tungsten wire, while the outer coil is made of a less radiopaque material, for example, MP35-N, or vice versa.

In the embodiment shown, the inner coil 90 is disposed about the distal guidewire section 16 from about the middle of the constant diameter section 35, about the ribbon 58, and to a position adjacent the tip portion 69. The coil 90 is attached to the outer coil 80 at proximal attachment point 93 using any suitable attachment technique, for example soldering, brazing, welding, adhesive bonding, friction fitting, or the like. The distal end 97 of the coil 90 is free of attachment. However, in other embodiments, distal end 97 of the coil 90 can be attached to the outer coil 80, or can be attached to other structure, for example, to the tip portion 69, to a centering or attachment ring, or other such structure. In some particular embodiments, the inner coil 90 is attached only to the outer coil 80 at one or more attachment points, and is essentially free of any other connection to a core wire, or in some cases, is free of connection to any other structure in the guidewire 10 other than the outer coil 80. Additionally, the inner coil 90 can be attached to the outer coil 80 along the entire length of the inner coil 90, or only along a portion of the length thereof. For example, in the embodiment shown, the inner coil 90 is attached only at the proximally disposed attachment point 93. In other embodiments, the coil 90 may be attached using other arrangements, for example, a distally disposed attachment point, or a combination of proximally and distally disposed attachment points. Attachment of the inner coil 90 to the outer coil 80 can be achieved using any suitable attachment technique, for example soldering (e.g. LASER diode soldering), brazing, welding, adhesive bonding, friction fitting, or the like.

Although attachment of the inner coil 90 to the outer coil 80 can be made in any suitable manner, as discussed above, in some embodiments, attachment of the inner coil 90 to the outer coil 80 can be achieved using a welding process, for example, LASER or plasma welding. Any of the above described material, structure, techniques or equipment can be used. As described above, in LASER welding, a light beam is used to supply the necessary heat. LASER welding can be beneficial in the processes contemplated by the invention, as the use of a LASER light heat source can provide pinpoint accuracy. It should also be understood that such LASER welding can also be used to attach other components of the guidewire, as discussed above.

In some embodiments, the attachment of the inner coil 90 to the outer coil 80 can extend around the entire circumference of the coils 80 and 90. In some other embodiments, however, one or more spaced connection points that do not extend all the way around the circumference of the coils 80 and 90 can be made. The use of certain attachment techniques, for example laser welding or laser diode soldering, or the like, can be useful in making connections around only a portion of the circumference coils 80 and 90 because they tend to allow the accuracy needed to make such connections. In some embodiments, connections around only a portion of the circumference of the coils 80 and 90 can allow for some desired characteristics, such as increased flexibility of the coils 80 and 90.

It will be understood by those of skill in the art and others that a broad variety of materials, dimensions, and structures can be used to construct suitable embodiments, depending upon the desired characteristics. The following examples are included by way of example only, and are not intended to be limiting. The inner coil 90 can be in the range of about 0.1 to about 3 inches long, and is made of rounded wire having a diameter of about 0.001 to about 0.005 inches. The coil 90 can have an outer diameter that is generally constant, and is in the range of about 0.002 to about 0.015 inches. The inner diameter of the coil can also be generally constant, and is in the range of about 0.001 to about 0.008 inches. The pitch of the coil 90 can be in the range of about 0.0005 to about 0.04 inches.

As discussed above, in some particular embodiments, the inner coil 90 is attached only to the outer coil 80 at one or more attachment points, and is essentially free of any other connection to a core wire, or in some cases, is free of connection to any other structure in the guidewire 10. Some such embodiments can provide the benefit of one or more additional coils, for example coil 90, disposed within the guidewire structure without the need to attach such coils to a shaft or core wire. For example, in some cases, it may be undesirable to attach additional structures to a core or shaft portion of a guidewire due to the possible changes in the flexibility or other characteristics at an attachment point. Thus, it may be desirable to avoid such attachment points, and attach any additional coils to a coil that is attached to the core wire or shaft, such as the outer coil 80.

Figure 9:
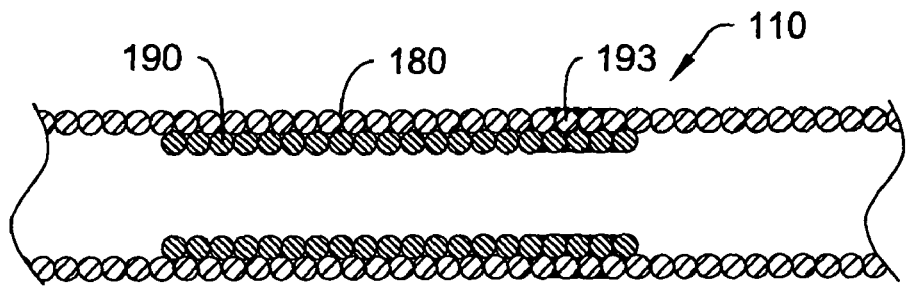
FIG. 9 is a cross sectional fragmentary view of an example coil construction that can be used in medical devices, the coil construction including an inner coil attached to an outer coil.

Such an arrangement of an inner coil being attached only to an outer coil could be used in a broad variety of medical devices. For example, refer now to FIG. 9, which is a cross sectional fragmentary view of an example coil construction 110 that can be used in medical devices which is very similar to that described above with regard to FIG. 1. The coil construction 110 includes an inner coil 190 attached to an outer coil 180 at one or more attachment points, for example, attachment point 193. The two coil members 180 and 190 can be made of the same materials, and have the same general construction and pitch spacing as discussed above with regard to the outer coil 80 and inner coil 90. In some other embodiments, additional coil members could be connected to the outer coil 180. In yet other embodiments, the inner coil 190 could be configured for attachment to a medical device, such as a guidewire, and one or more outer coils 180 could be attached to the inner coil 190, and be essentially free of any other attachment to the medical device. Any such coil arrangement could be incorporated into a medical device construction by attaching only one of the coils to the medical device, while the other coils could be essentially free of any other attachment other than to the coil that is attached to the medical device. The attachment of the coil members, for example 180 and 190, to one another can be achieved using any suitable attachment technique, for example soldering, brazing, welding, adhesive bonding, friction fitting, or the like, wherein in some embodiments, welding, such as LASER or plasma welding are particularly used.

Figure 10:
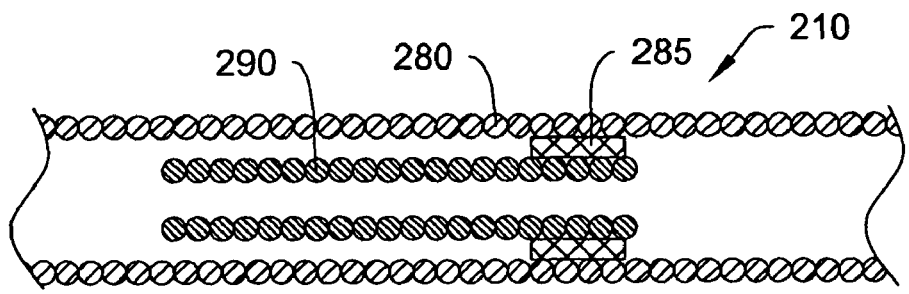
FIG. 10 is a cross sectional fragmentary view of another example embodiment of a coil construction wherein an inner coil is connected to an outer coil via an intermediate member.

Refer now to FIG. 10, which is an alternative embodiment of a coil construction 210 including an inner coil 290 attached to an outer coil 280 by an intermediate attachment member 285 that interconnects the two coil members 280 and 290. The two coil members 280 and 290 can be made of the same materials, and have the same general construction and pitch spacing as discussed above with regard to the outer coil 80 and inner coil 90. The intermediate member 285 can be any structure generally disposed between and being connected to the two coil members 280 and 290. In some embodiments, the intermediate structure 285 can be a generally tubular structure disposed around inner coil 290, and disposed within outer coil 280. However, a broad variety of other structures could be used. The intermediate structure 285 may be made of a variety of materials including metals, metal alloys, polymers, and the like, including those described above with regard to the guidewire sections 14/16, the connector 18, the ribbon 58, and the coils 180 and 190. In some embodiments, the intermediate structure 285 can be made of, coated or plated with, or otherwise include a radiopaque material and/or can include materials or structure to impart a degree of MRI compatibility, as discussed above in relation to the guidewire sections 14/16, the connector 18, the ribbon 58 and the coils 180 and 190. The attachment of the coil members, for example 280 and 290, to the intermediate member 285 can be achieved using any suitable attachment technique, for example soldering, brazing, welding, adhesive bonding, friction fitting, or the like, wherein in some embodiments, welding, such as LASER or plasma welding are particularly used.

Figure 11:
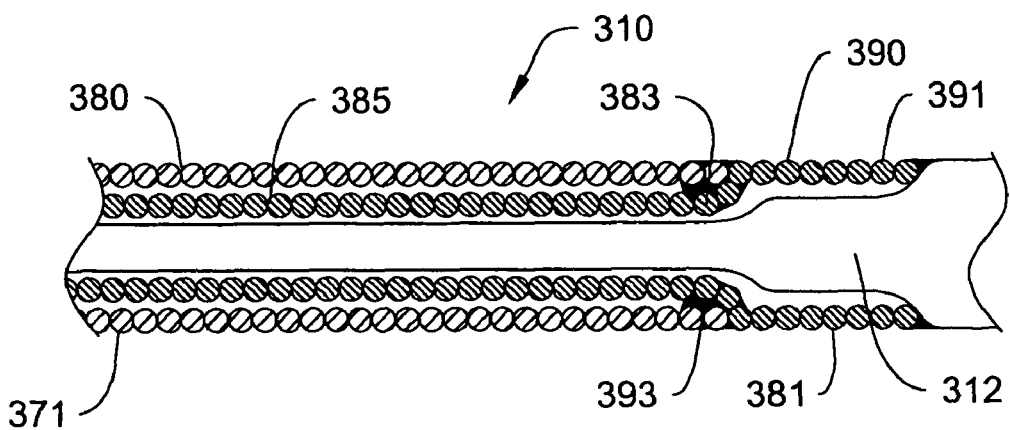
FIG. 11 is a cross sectional fragmentary view of an another example coil construction that can be used in medical devices, the coil construction including a first coil attached to a second coil.

Refer now to FIG. 11, which shows another alternative coil construction 310 including a first coil 390 attached to a second coil 380 at an attachment point 393. The first coil 390 could be adapted or configured for attachment to a medical device, for example, for attachment to a core wire or shaft 312 of a guidewire. For example, a proximal portion 391 of the first coil 390 could be attached to a core wire or shaft 312, and the core wire or shaft 312 could extend within the lumen of the first coil 390. The first coil 390 could include a first constant diameter portion 381, a tapered portion 383, and a second, narrower, constant diameter portion 385. The second coil 380 could be adapted or configured to extend about at least a portion of the tapered portion 383, and the second, narrower, constant diameter portion 385. The attachment point 393 could be adjacent the tapered portion 383. Additionally, the second coil 390 could be essentially free of attachment to any other portion of the guidewire other than the first coil 380. In such embodiments, a distal portion 371 of the second coil 390 could be free, or could be attached to the first coil 380 at a point more distally than is shown. In other embodiments, however, it is contemplated that the distal portion 371 of the second coil 390 could be connected to other structure.

Figure 12:
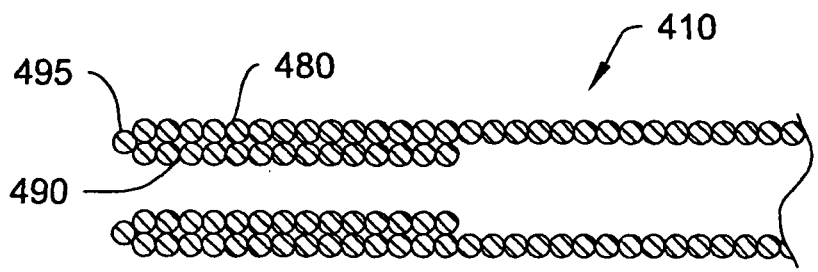
FIG. 12 is a cross sectional fragmentary view of an example coil configuration that can be used in medical devices, the coil configuration including an inner portion and an outer portion.

Refer now to FIG. 12, which shows another alternative coil construction 410 including a coil 489 including a first inner portion 490 and a second outer portion 480. In this embodiment, the coil 489 is a continuous filament that has been wound into the coil construction including the inner and outer portions 490/480. For example, such a coil construction can be achieved by first winding a coil filament to create the inner portion 490 at a desired diameter, and then reversing the winding of the filament so as to wind the filament around the inner portion 490 to form the outer portion 480. The point of reversal could form a tip portion 495. Such a winding technique could be accomplished using standard coil winding equipment. Additionally, in some embodiments, the two coil portions 480 and 490 can be attached to each other at one or more point or portion along the length of the coil 490, or along the entire length of the coil 490. Such attachment can be made using any suitable attachment technique, for example soldering, brazing, welding, adhesive bonding, friction fitting, or the like, wherein in some embodiments, welding, such as LASER or plasma welding are particularly used. The two coil portions 480 and 490 can be made of the same materials, and have the same general construction and pitch spacing as discussed above with regard to the outer coil 80 and inner coil 90.

Figure 13:
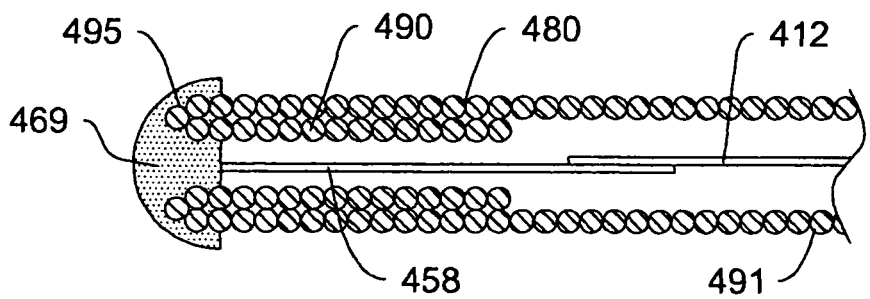
FIG. 13 is a cross sectional fragmentary view of a tip construction of a guidewire including the coil configuration of FIG. 12.

As seen in FIG. 13, such a coil construction 410 can be incorporated into a medical device, for example, for attachment to a core wire or shaft 412 of a guidewire. For example, the tip portion 495 of the coil construction 410 could be attached to a distal tip structure 469 of a guidewire, which in turn is attached to a ribbon 458 which in turn is attached to the core wire or shaft 412. In such embodiments, a proximal portion 491 of the outer portion 480 could be free, or could be attached to other structure, for example, to the core wire or shaft 412 at a point more proximally than is shown.

Figure 2:
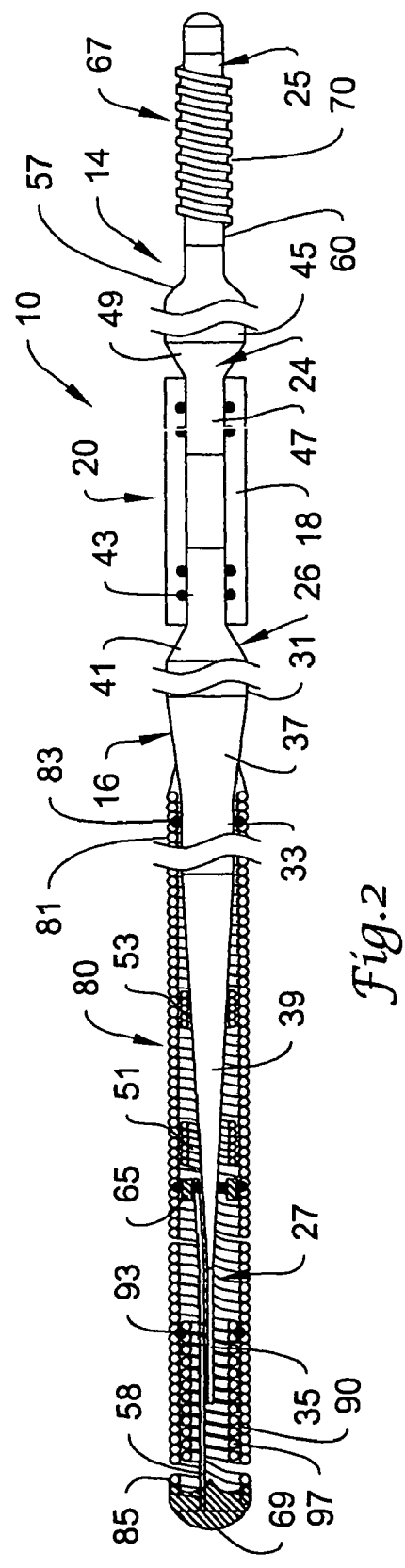
FIG. 2 is a cross sectional fragmentary view of another example embodiment of a guidewire.

Refer now to FIG. 2, which shows a guidewire 10 very similar to that shown in FIG. 1, wherein like reference numerals indicate similar structure as discussed above. The proximal/distal guidewire sections 14/16, the connection 20, the joint 12, and the tubular connector 18 shown in the embodiment of FIG. 2 can also include the same general construction, structure, materials, and methods of construction as discussed above with regard to like components in the embodiments of FIG. 1. The distal tip portion of the guidewire 10 of FIG. 2 is also very similar to that shown in FIG. 1, wherein like reference numerals indicate similar structure. In the embodiment shown in FIG. 2, however, two radiopaque marker members 51 and 53 are attached to the distal guidewire section 16. The markers 51 and 53 are made of, are coated or plated with, or otherwise include radiopaque materials that are capable of producing a relatively bright image on a fluoroscopy screen or another imaging technique during a medical procedure, as discussed above. Such markers 51 and 53 can be structures such as bands, coils, and the like, and can be attached to the proximal or distal sections 14/16 in any suitable attachment technique, for example, soldering, brazing, welding, adhesive bonding, friction fitting, or the like. Additionally, in some embodiments, the distal guidewire section 16 can include constant diameter portions chat are ground or otherwise formed therein for placement of the markers. Additionally, the position of the markers 51 and 53 in relation to other structures within the guidewire can vary widely, depending upon the desired ability to image the guidewire at certain points along the length thereof.

It will be understood by those of skill in the art and others that a broad variety of materials, dimensions, and structures can be used to construct suitable embodiments, depending upon the desired characteristics. The following examples are included by way of example only, and are not intended to be limiting. The markers 51 and 53 can be coiled members in the range of about 0.03 to about 2 inches long, and is made of rounded radiopaque wire (e.g. platinum/tungsten wire) having a diameter of about 0.0005 to about 0.005 inches. The markers 51 and 53 can be positioned along the length of the guidewire to achieve the desired imaging effect. In some embodiments, the inner coil 90 is radiopaque, and is about 2 cm long, the marker 51 is about 0.5 cm long, and is positioned about 1.5 cm from the proximal end of the inner coil 90, and the marker 53 is about 0.5 cm long, and is positioned about 1.5 cm from the proximal end of the marker 51. It should be understood that a broad variety of marker configurations can be used, including more or fewer marker members.

The embodiment shown in FIG. 2 also includes structure 67 adapted to mate with an extension wire (not shown) disposed near the proximal end 25 of the proximal section 14. The structure 67 can include a tapering portion 57 and a constant diameter portion 60. The constant diameter portion 60 can include a threaded portion 70 that is formed therein, or attached thereto. In some embodiments, the threaded portion 70 includes a coiled ribbon or wire that is attached to the constant diameter portion 60 using a suitable attachment technique, for example, soldering, brazing, welding, adhesive bonding, friction fitting, or the like.

It should be understood that in some other embodiments, different tip configurations can be used. For example, some embodiments can include a polymer jacket tip (optionally covering connection 20) or combination of a flexible coil tip and/or jacket tip.

Figure 15:
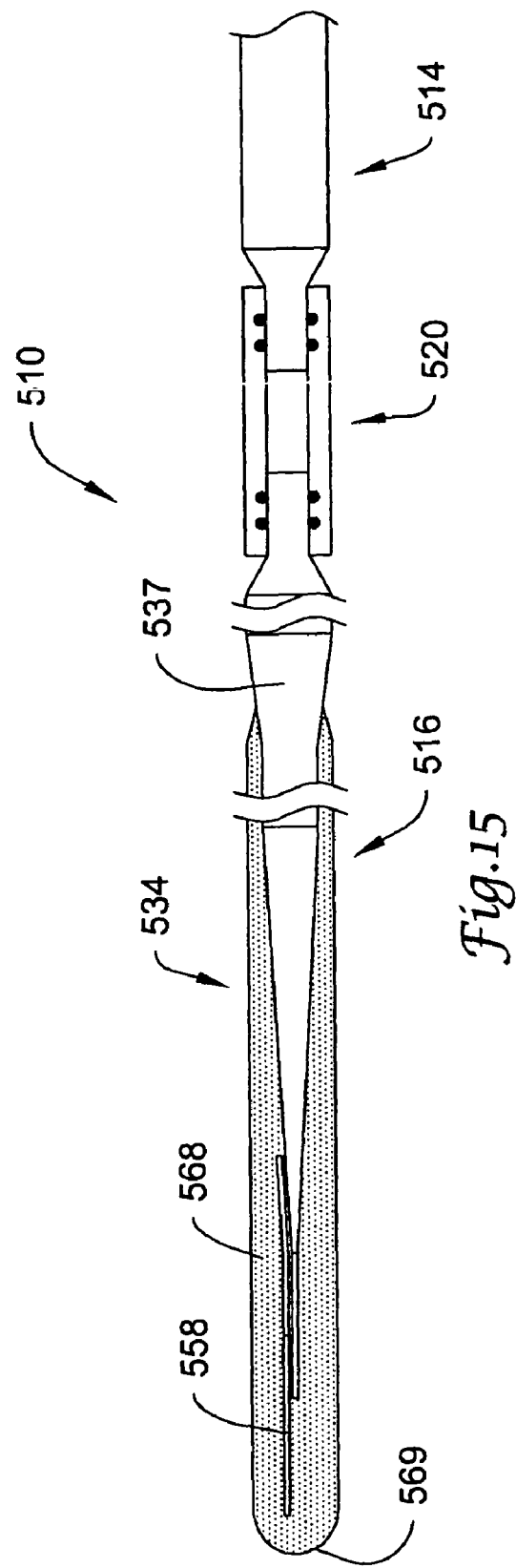
FIG. 15 is a partial cross sectional fragmentary view of a guidewire in accordance with another example embodiment.

For example, refer now to FIG. 15, which shows a guidewire 510 including an outer sleeve 568 is disposed about the distal end portion 534 of the distal guidewire section 516. In the embodiment shown, the sleeve 568 extends from the tapered region 537 to beyond the distal most portion of the ribbon 558, and forms a rounded tip portion 569. In other embodiments, the sleeve 558 can extend further in a proximal direction, and in some cases can extend over the connection 520, or over the proximal guidewire section 514. In yet other embodiments, the sleeve 568 can begin at a point distal of the tapered region 537.

Suitable materials for use as the outer sleeve 568 include any material that would give the desired strength, flexibility or other desired characteristics. Some suitable materials include polymers, and like material. Examples of suitable polymer material include any of a broad variety of polymers generally known for use as guidewire polymer sleeves. The use of a polymer for outer sleeve 568 can serve several functions. The use of a polymer sleeve can improve the flexibility properties of the distal portion of the guidewire. Choice of polymers for the sleeve 568 will vary the flexibility. For example, polymers with a low durometer or hardness will make a very flexible or floppy tip. Conversely, polymers with a high durometer will make a tip which is stiffer. The use of polymers for the sleeve can also provide a more atraumatic tip for the guide wire. An atraumatic tip is better suited for passing through fragile body passages. Finally, a polymer can act as a binder for radiopaque materials, as discussed in more detail below.

In some embodiments, the polymer material used is a thermoplastic polymer material. Some examples of some suitable materials include polyurethane, elastomeric polyamides, block polyamide/ethers (such as Pebax), silicones, and co-polymers. The sleeve may be a single polymer, multiple layers, or a blend of polymers. By employing careful selection of materials and processing techniques, thermoplastic, solvent soluble, and thermosetting variants of these materials can be employed to achieve the desired results.

The sleeve 568 can be disposed around and attached to the guidewire 510 using any suitable technique for the particular material used. In some embodiments, the sleeve 568 is attached by heating a sleeve of polymer material to a temperature until it is reformed around the distal guidewire section 516 and the ribbon 558. In some other embodiments, the sleeve 568 can be attached using heat shrinking techniques. The sleeve 568 may be finished, for example, by a centerless grinding or other method, to provide the desired diameter and to provide a smooth outer surface.

In some embodiments, the sleeve 568, or portions thereof, can include, or be doped with, radiopaque material to make the sleeve 568, or portions thereof, more visible when using certain imaging techniques, for example, fluoroscopy techniques. Any suitable radiopaque material known in the art can be used. Some examples include precious metals, tungsten, barium subcarbonate powder, and the like, and mixtures thereof. In some embodiments, the sleeve 568 can include different sections having different amounts of loading with radiopaque material. In some embodiments, it is also contemplated that a separate radiopaque member or a series of radiopaque members, such as radiopaque coils, bands, tubes, or other such structures could be attached to the guidewire 510, and be attached to the guidewire 510 or disposed within the sleeve 568.

Some examples of other suitable tip constructions and structures that can be used are disclosed in U.S. Publication Nos. 2003/0069520 A1 and 2003/0069521 A1, which are incorporated herein by reference.

Additionally, in some embodiments, a coating, for example a lubricious (e.g., hydrophilic) or other type of coating may be applied over portions or all of the medical devices or structures discussed above. For example, such a coating may be applied over portions or all of the guidewire 10, including, for example, guidewire sections 14/16, the connector 18, the coil 80, the distal tip 69, sleeve 568, or other portions of the guidewire 10. Hydrophobic coatings such as fluoropolymers, silicones, and the like provide a dry lubricity which improves guide wire handling and device exchanges. Lubricious coatings improve steerability and improve lesion crossing capability. Suitable lubricious polymers are well known in the art and may include hydrophilic polymers such as, polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference. In some embodiments, the more distal portion of the guidewire is coated with a hydrophilic polymer as discussed above, and the more proximal portion is coated with a fluoropolymer, such as polytetrafluroethylene (PTFE).

It should be understood that this disclosure is, in many respects, only illustrative. Changes may be made in details, particularly in matters of shape, size, and arrangement of steps without exceeding the scope of the invention. For example, alternative structure can be used in connecting the proximal and distal sections of guidewires. Additionally, alternative tip constructions including a flexible coil tip, a polymer jacket tip, a tip including a coiled safety/shaping wire, or combination thereof, and other such structure may be placed on the guidewire. The invention's scope is, of course, defined in the language in which the appended claims are expressed.

What is claimed is:

1. A method of making a guidewire, the method comprising:
   providing a metallic elongated guidewire shaft;
   providing a metallic structural member configured to be connected to the elongated guidewire shaft;
   disposing the structural member adjacent the elongated shaft in a predetermined position;
   disposing a heat activated attachment material adjacent the elongated shaft and the structural member, the heat activated attachment material comprising solder or brazing material;
   directly heating the heat activated attachment material using LASER energy such that the heat activated attachment material adjoins the elongated shaft and the structural member; and
   allowing the heat activated attachment material to cool and attach the elongated shaft and the structural member.

2. The method of claim 1, wherein the activated attachment material comprises a solder material.

3. The method of claim 1, wherein the heat activated material comprises a brazing material.

4. The method of claim 1, wherein a LASER diode is used to heat the heat activated attachment material.

5. The method of claim 1, wherein the structural member comprises a ribbon.

6. The method of claim 1, wherein the structural member comprises a wire.

7. The method of claim 1, wherein the structural member comprises a coil.

8. The method of claim 1, wherein the elongated shaft comprises a nickel-titanium alloy.

9. The method of claim 1, wherein the elongated shaft comprises a stainless steel alloy.

10. The method of claim 1, wherein the structural member comprises stainless steel, nickel-titanium alloy, nickel-chromium alloy, nickel-chromium-iron alloy, cobalt alloy, tungsten, platinum, gold, a metal alloy having a Unified Numbering System (UNS) designation of R30035, a metal alloy having a Unified Numbering System (UNS) designation of N06022, a metal alloy having a Unified Numbering System (UNS) designation of N04400, or a metal alloy having a Unified Numbering System (UNS) designation of N06625.

11. The method of claim 1, wherein at least a portion of the heat activated attachment material after heating is disposed between the elongated shaft and the structural member.

12. The method of claim 1, wherein the elongated guidewire shaft includes a proximal portion and a distal portion, and the structural member is attached to the distal portion of the shaft.

13. A method of making a guidewire, the method comprising:
   providing an elongated guidewire shaft including a distal section and a proximal section;
   providing a coil member configured to be connected to the elongated shaft, the coil member having a circumference;
   connecting the coil member to the distal section of the elongated shaft using a heat activated attachment material comprising solder or brazing material, wherein LASER energy is used to directly heat the heat activated attachment material;
   wherein the coil member is connected to the elongated shaft around only a portion of the circumference of the coil.

14. A method of making a guidewire, the method comprising:
   providing an elongated guidewire shaft including a distal section and a proximal section;
   providing a ribbon member configured to be connected to the elongated shaft;
   connecting the ribbon member to the distal section of the elongated shaft using a heat activated attachment material comprising solder or brazing material, wherein LASER energy is used to heat the heat activated attachment material used to connect the ribbon member to the distal section of the elongated shaft.

15. A method of making a guidewire, the method comprising:
   providing an elongated guidewire shaft including a distal section and a proximal section;
   providing a tubular member configured to be connected to the elongated shaft;
   connecting the tubular member to the distal section of the elongated shaft using a heat activated attachment material comprising solder or brazing material, wherein LASER energy is used to heat the heat activated attachment material used to connect the tubular member to the distal section of the elongated shaft.

* * * * *

UNITED STATES PATENT AND TRADEMARK OFFICE
CERTIFICATE OF CORRECTION

| | |
|---|---|
| PATENT NO. | : 8,222,566 B2 |
| APPLICATION NO. | : 11/058393 |
| DATED | : July 17, 2012 |
| INVENTOR(S) | : Brice L. Shireman et al. |

Page 1 of 1

It is certified that error appears in the above-identified patent and that said Letters Patent is hereby corrected as shown below:

Column 5
Line 7, delete "14/15", and insert therefor -- 14/16 --.

Signed and Sealed this
Second Day of October, 2012

David J. Kappos
*Director of the United States Patent and Trademark Office*